(12) United States Patent
Mak et al.

(10) Patent No.: US 10,588,512 B2
(45) Date of Patent: Mar. 17, 2020

(54) OPTICAL COHERENCE TOMOGRAPHY SYSTEM WITH DUAL OPTICAL COHERENCE TOMOGRAPHY PROBES

(71) Applicants: Siu Wai Jacky Mak, Toronto (CA); Michael Frank Gunter Wood, Toronto (CA)

(72) Inventors: Siu Wai Jacky Mak, Toronto (CA); Michael Frank Gunter Wood, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 124 days.

(21) Appl. No.: 14/892,122

(22) PCT Filed: Mar. 11, 2015

(86) PCT No.: PCT/IB2015/051777
§ 371 (c)(1),
(2) Date: Nov. 18, 2015

(87) PCT Pub. No.: WO2016/142748
PCT Pub. Date: Sep. 15, 2016

(65) Prior Publication Data
US 2017/0079529 A1    Mar. 23, 2017

(51) Int. Cl.
*A61B 5/00* (2006.01)
*A61B 90/00* (2016.01)
*A61B 3/10* (2006.01)

(52) U.S. Cl.
CPC .............. *A61B 5/0066* (2013.01); *A61B 5/00* (2013.01); *A61B 5/7425* (2013.01); *A61B 3/102* (2013.01);
(Continued)

(58) Field of Classification Search
None
See application file for complete search history.

(56) References Cited

U.S. PATENT DOCUMENTS 6,485,413 B1 * 11/2002 Boppart ............. A61B 1/00096
356/450
8,232,799 B2    7/2012 Hajian et al.
(Continued)

FOREIGN PATENT DOCUMENTS

WO    2006003551 A1    1/2006
WO    2013157006 A1    10/2013

OTHER PUBLICATIONS

Baumann et al, "Swept source / Fourier domain polarization sensitive optical coherence tomography with a passive polarization delay unit", Apr. 23, 2012 / vol. 20, No. 9 / Optics Express.*
(Continued)

*Primary Examiner* — Jonathan Cwern
(74) *Attorney, Agent, or Firm* — Perry + Currier, Inc.

(57) ABSTRACT

An optical coherence tomography (OCT) system with dual optical coherence tomography probes is provided comprising: an optical scope comprising a distal end; a first OCT probe; and, a second OCT probe, each of the first OCT probe and the second OCT probe mechanically attached to the optical scope, the first OCT probe and the second OCT probe being substantially paraxial and configured to focus on a same scanning area, the optical scope configured to optically image the same scanning area using the distal end, the first OCT probe having a higher resolution than the second OCT probe.

13 Claims, 13 Drawing Sheets

(52) U.S. Cl.
CPC ........... *A61B 5/0042* (2013.01); *A61B 5/0073* (2013.01); *A61B 90/00* (2016.02); *A61B 2090/3735* (2016.02); *A61B 2505/05* (2013.01); *A61B 2562/043* (2013.01); *A61B 2576/00* (2013.01)

(56) References Cited

U.S. PATENT DOCUMENTS

| | | | |
|---|---|---|---|
| 8,767,217 B2 | 7/2014 | Hajian et al. | |
| 2005/0182295 A1* | 8/2005 | Soper | A61B 1/0008 600/117 |
| 2007/0076217 A1* | 4/2007 | Baker | A61B 3/1005 356/498 |
| 2007/0274650 A1* | 11/2007 | Tearney | A61B 1/00082 385/118 |
| 2008/0062401 A1* | 3/2008 | Bakker | G01N 21/65 356/51 |
| 2008/0260342 A1* | 10/2008 | Kuroiwa | A61B 5/0066 385/133 |
| 2010/0228238 A1* | 9/2010 | Brennan | A61B 5/0066 606/13 |
| 2010/0284021 A1* | 11/2010 | Hacker | A61B 3/102 356/497 |
| 2011/0026035 A1* | 2/2011 | Muto | A61B 3/102 356/456 |
| 2012/0245473 A1* | 9/2012 | Mycek | A61B 5/0071 600/479 |
| 2014/0192323 A1* | 7/2014 | Kakuma | A61B 3/102 351/206 |
| 2015/0201833 A1* | 7/2015 | Chong | A61B 3/102 351/206 |

OTHER PUBLICATIONS

International Search Report, dated Nov. 6, 2015, PCT/IB2015/051777.
CIPO, Examination Report, dated Jun. 1, 2018, re Canadian Patent Application No. 2979149.
International Preliminary Report on Patentability dated Sep. 12, 2017, by ISA, re PCT International Patent Application No. PCT/IB2015/051777.

* cited by examiner

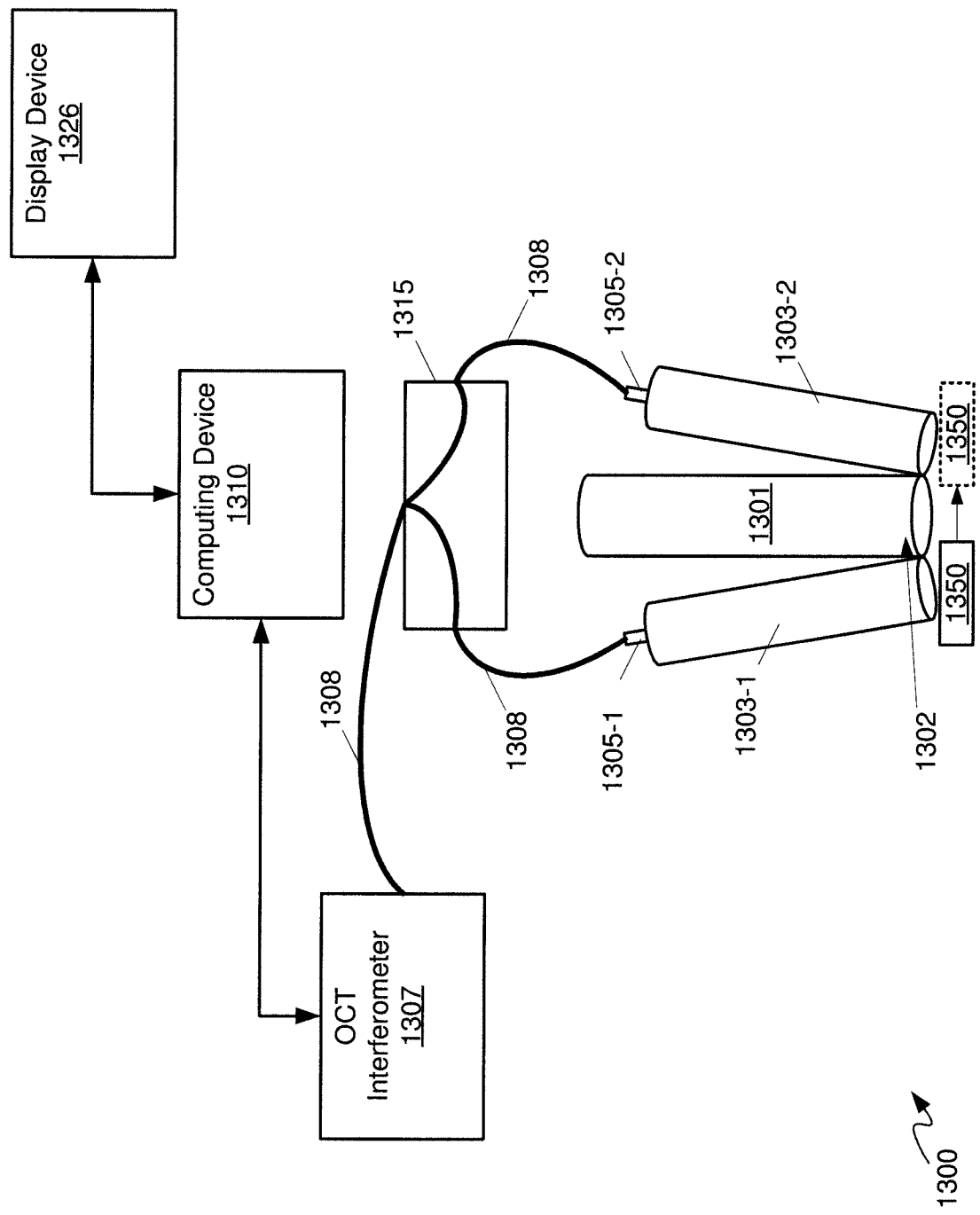

OPTICAL COHERENCE TOMOGRAPHY SYSTEM WITH DUAL OPTICAL COHERENCE TOMOGRAPHY PROBES

FIELD

The specification relates generally to optical coherence tomography and methods for minimally invasive therapy and image guided medical procedures, and specifically to an optical coherence tomography system with dual optical coherence tomography probes.

BACKGROUND

External surgical microscopes have been used to provide imaging of surgical fields with high resolution and high magnification. However, these images are limited to being two-dimensional. It is therefore difficult for some surgeons to visualize any depth information of the imaged tissue. It also does not provide any depth perception of the tools surgeons used in the field. Optical Coherence Tomography (OCT) enables imaging of tissue with depth limited to typically 1-3 mm due to the light absorption and scattering property of tissue.

SUMMARY

The present disclosure is generally directed to image guided medical procedures which may or may not use an access port. A port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Further, an OCT (Optical Coherence Tomography) is provided that includes an optical scope used external to an access port, and two paraxial OCT (Optical Coherence Tomography) probes, one of which has a higher resolution than the other such, and hence a smaller depth of field, such that depth information may be capture by imaging a same scanning area using both OCT probes together. The OCT probes are mechanically attached to the optical scope such that a surgeon, and the like, may switch between using the optical scope for optical imaging and using the OCT probes together with a display device for OCT imaging.

An aspect of the present specification provides An OCT (Optical Coherence Tomography) system comprising: an optical scope comprising a distal end; a first OCT probe; and, a second OCT probe, each of the first OCT probe and the second OCT probe mechanically attached to the optical scope, the first OCT probe and the second OCT probe being substantially paraxial and configured to focus on a same scanning area, the optical scope configured to image the same scanning area using the distal end, the first OCT probe having a higher resolution than the second OCT probe.

The optical scope may be configured the image the same scanning area through a surgical access port.

The optical scope, the first OCT probe and the second OCT probe may be configured for use with one or more of an image guided medical procedure, and a minimally invasive procedure.

The first OCT probe may have a smaller depth of field than the second OCT probe.

The first OCT probe may have a resolution in a range of about 0.1 µm to about 25 µm.

The first OCT probe may have a resolution in a range of about 1 µm to about 10 µm.

The second OCT probe may have a resolution in a range of about 10 µm to about 1 mm.

The second OCT probe may have a resolution in a range of about 25 µm to about 100 µm.

The OCT system may further comprise a first optical coupler, a second optical coupler, a first OCT interferometer and a second OCT interferometer, the first optical coupler configured to couple the first OCT probe to the first OCT interferometer, and the second optical coupler configured to couple the second OCT probe to the second OCT interferometer.

The OCT system may further comprise an optical coupler and an OCT interferometer, the optical coupler configured to switch between coupling the first OCT probe or the second OCT probe to the OCT interferometer. The optical coupler may comprise an optical rotary joint.

The OCT system may further comprise: an optical coupler, an OCT interferometer, and a switchable cover, the optical coupler configured to optically couple the first OCT probe and the second OCT probe to a same OCT interferometer, and the switchable cover configured to alternately cover the first OCT probe and the second OCT probe.

The OCT system may further comprise at least one illuminator configured to illuminate the same scanning area.

Each of the first OCT probe and the second OCT probe may be removable from the optical scope.

The first OCT probe and the second OCT probe may be attached on opposite sides of the optical scope.

The OCT system may further comprise a mechanical connector configured to attach one or more of the optical scope, the first OCT probe and the second OCT probe to a mechanical arm of a surgical system.

The OCT system may further comprise at least one computing device configured to combine output from each of the first OCT probe and the second OCT probe into combined output. The OCT system may further comprise at least one display device in communication with the computing device, the at least one display device configured to visually display the combined output from the first OCT probe and the second OCT probe.

The OCT system may further comprise a tracking device located at a proximal end of the OCT system, the tracking device configured to be tracked by a navigation system.

The OCT system may further comprise a device positioning system that positions the optical scope, the first OCT probe and the second OCT probe at a working distance from a tissue surface, the same scanning area comprising the tissue surface.

BRIEF DESCRIPTIONS OF THE DRAWINGS

For a better understanding of the various implementations described herein and to show more clearly how they may be carried into effect, reference will now be made, by way of example only, to the accompanying drawings in which:

FIG. 13 depicts an OCT system that includes a switchable cover, according to alternative non-limiting implementations.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
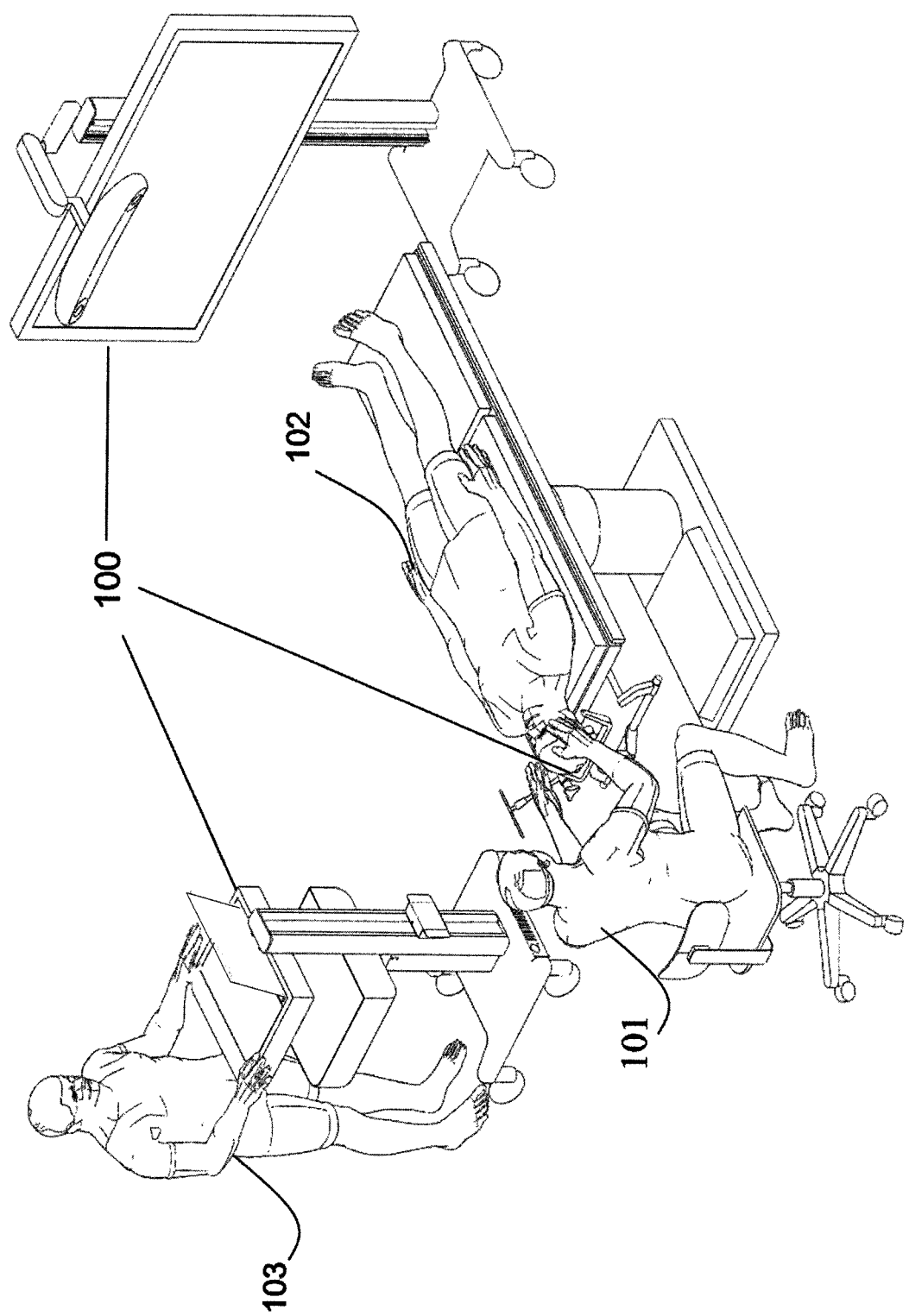
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery or surgical corridor-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
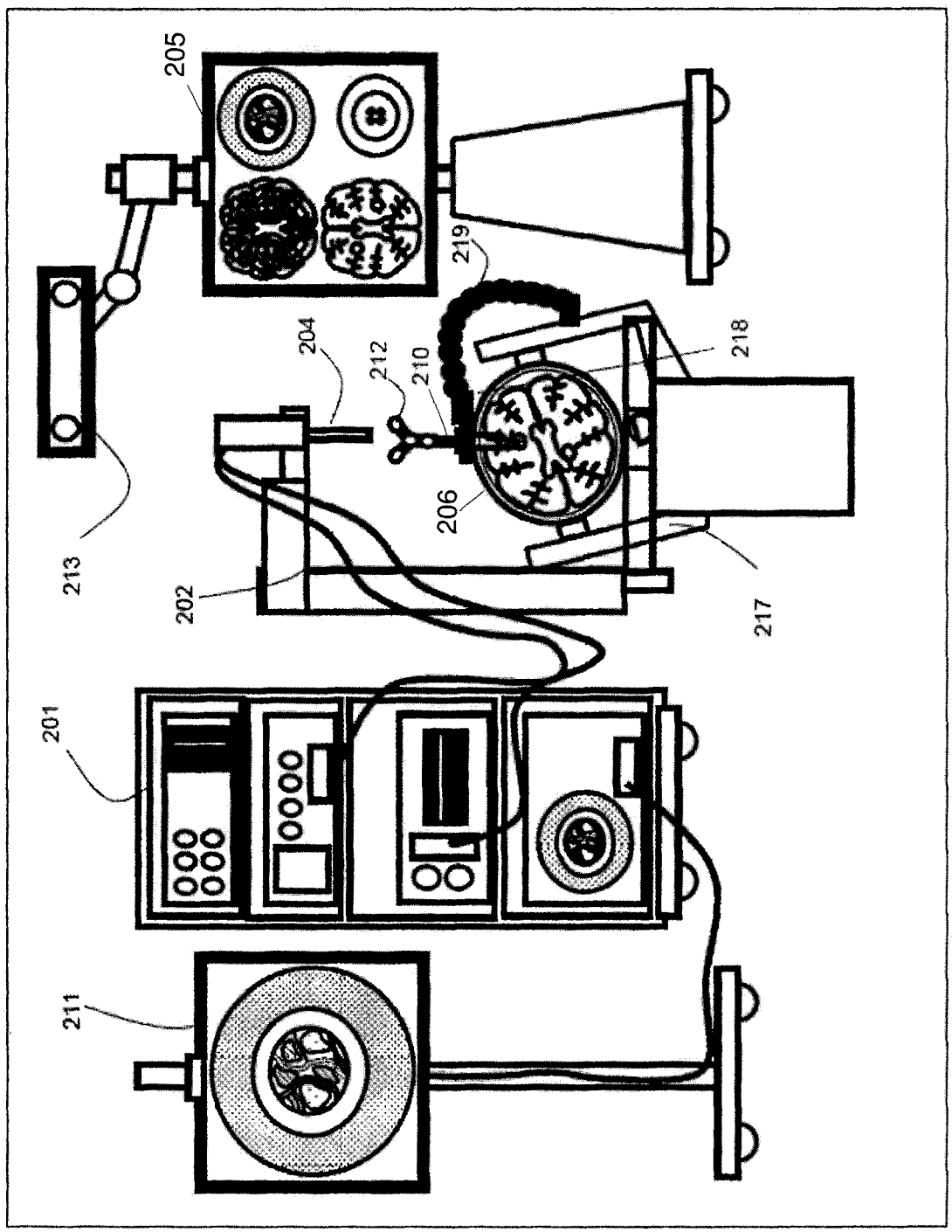
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
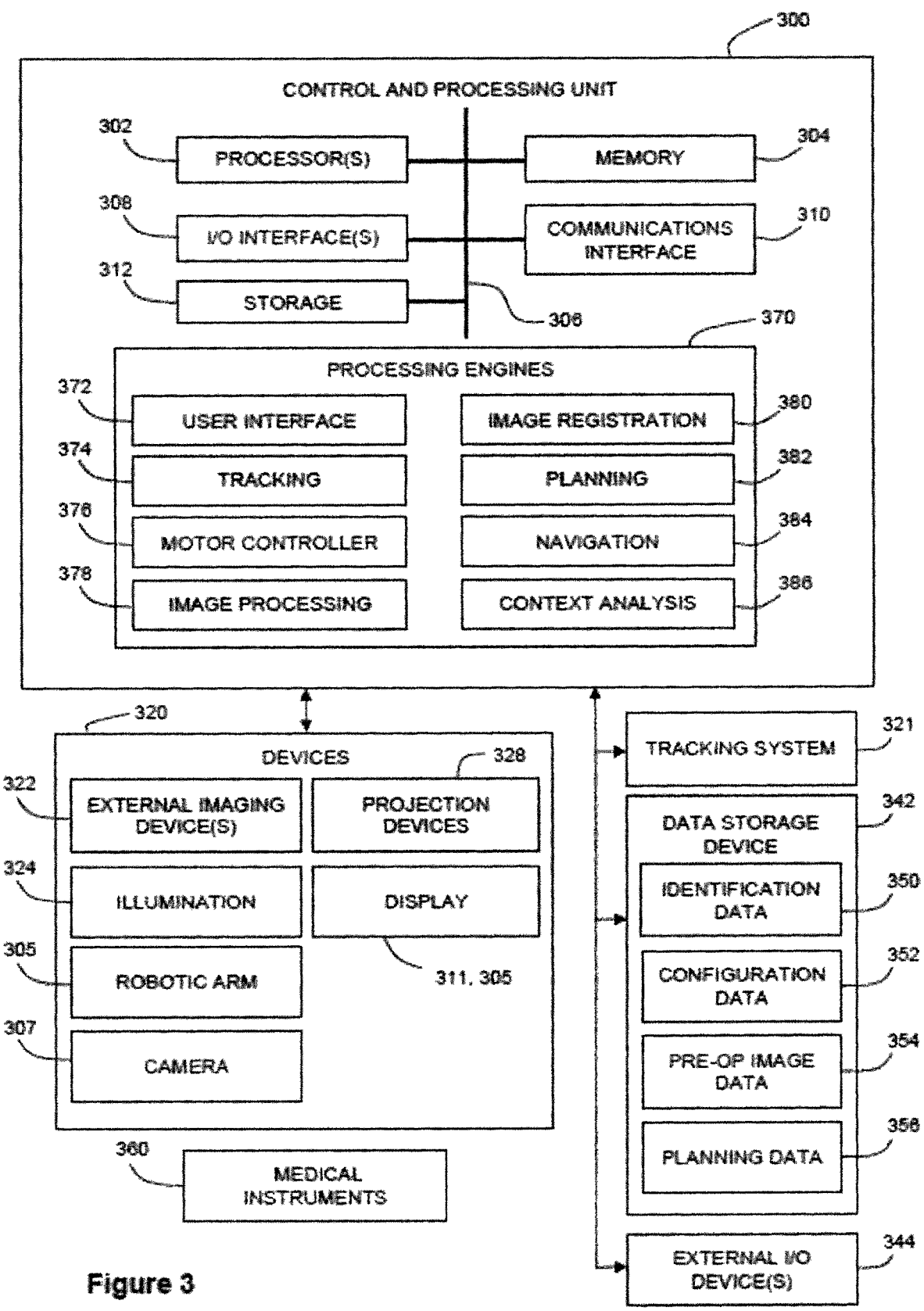
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
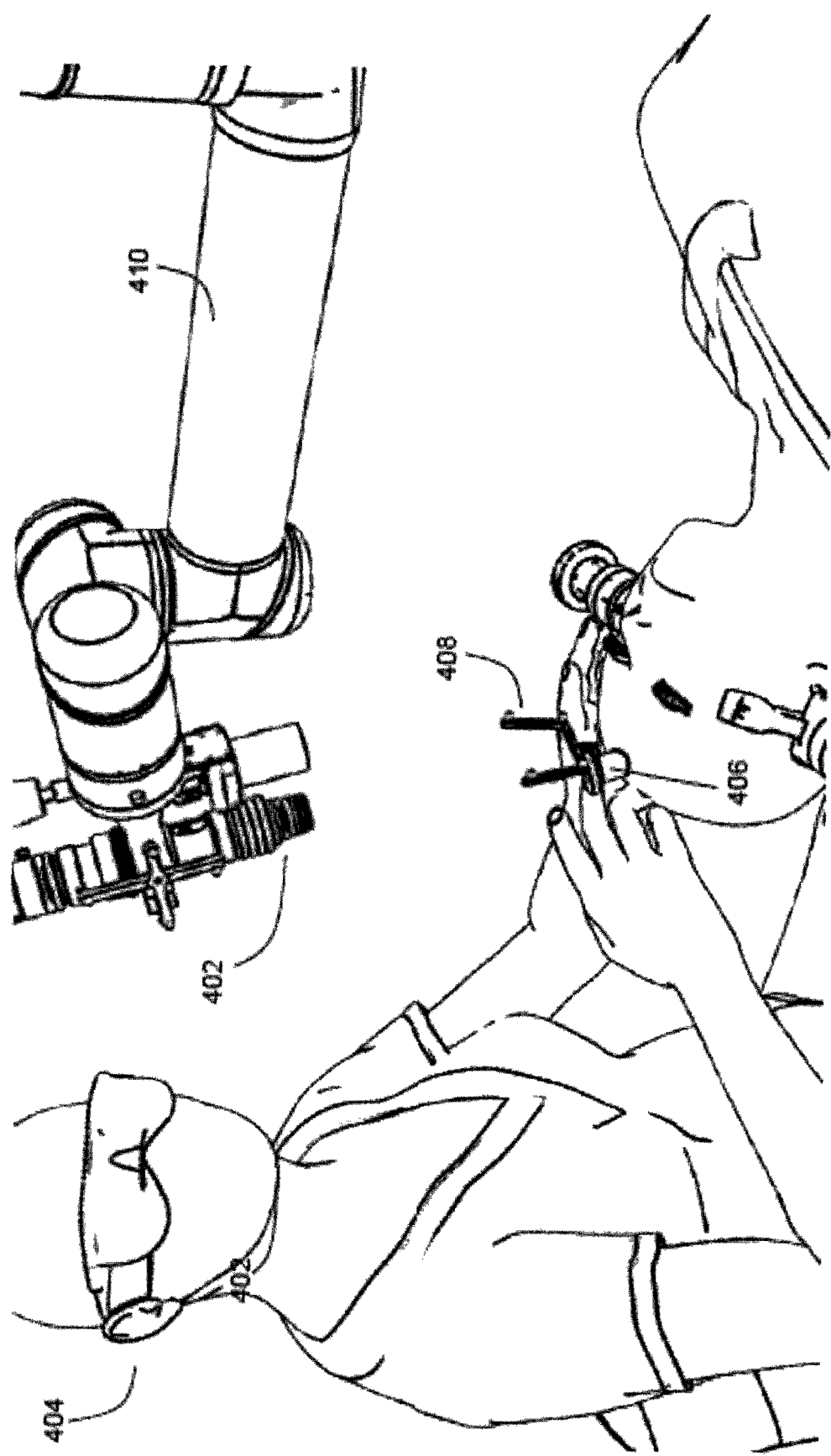
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
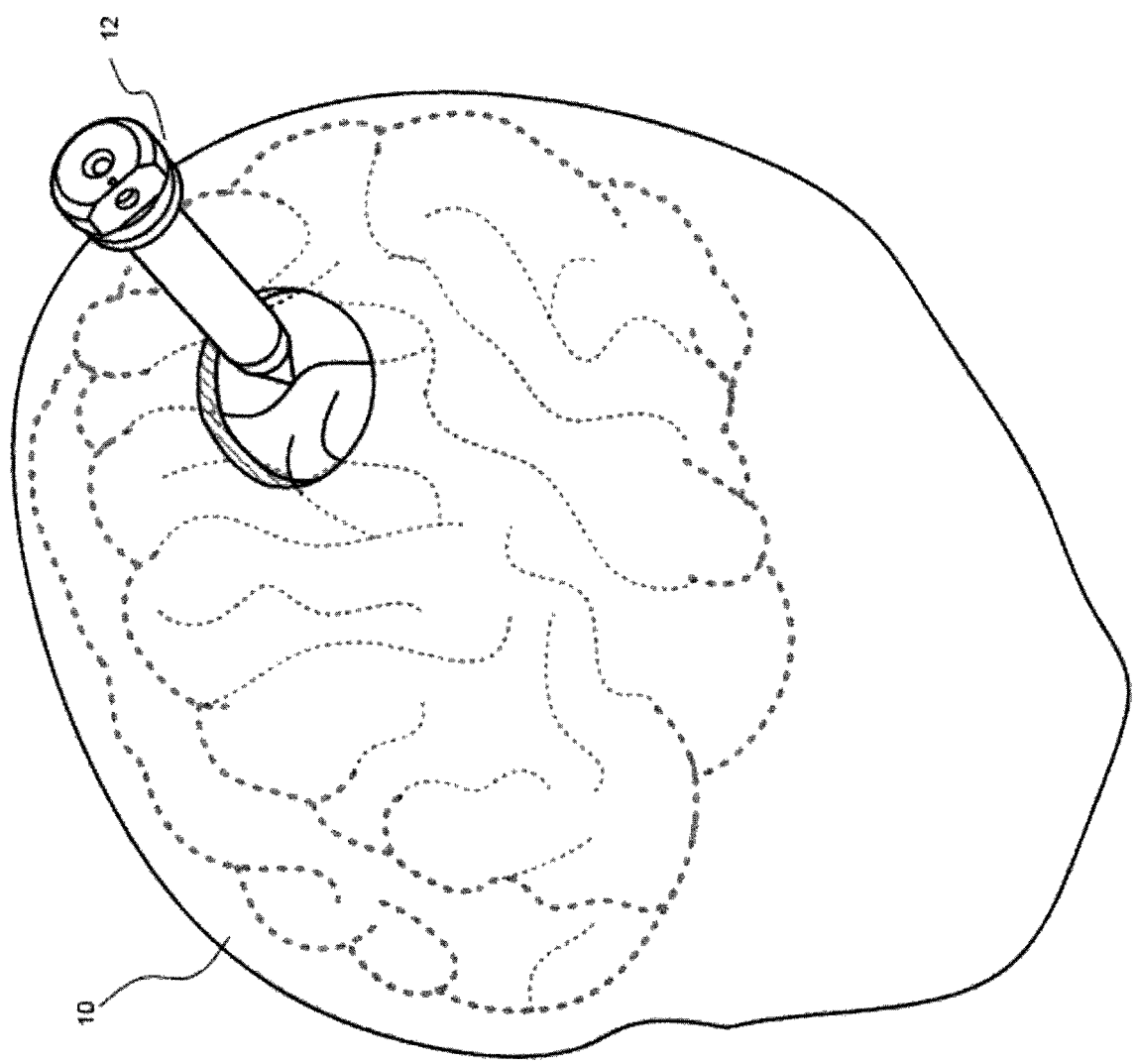
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
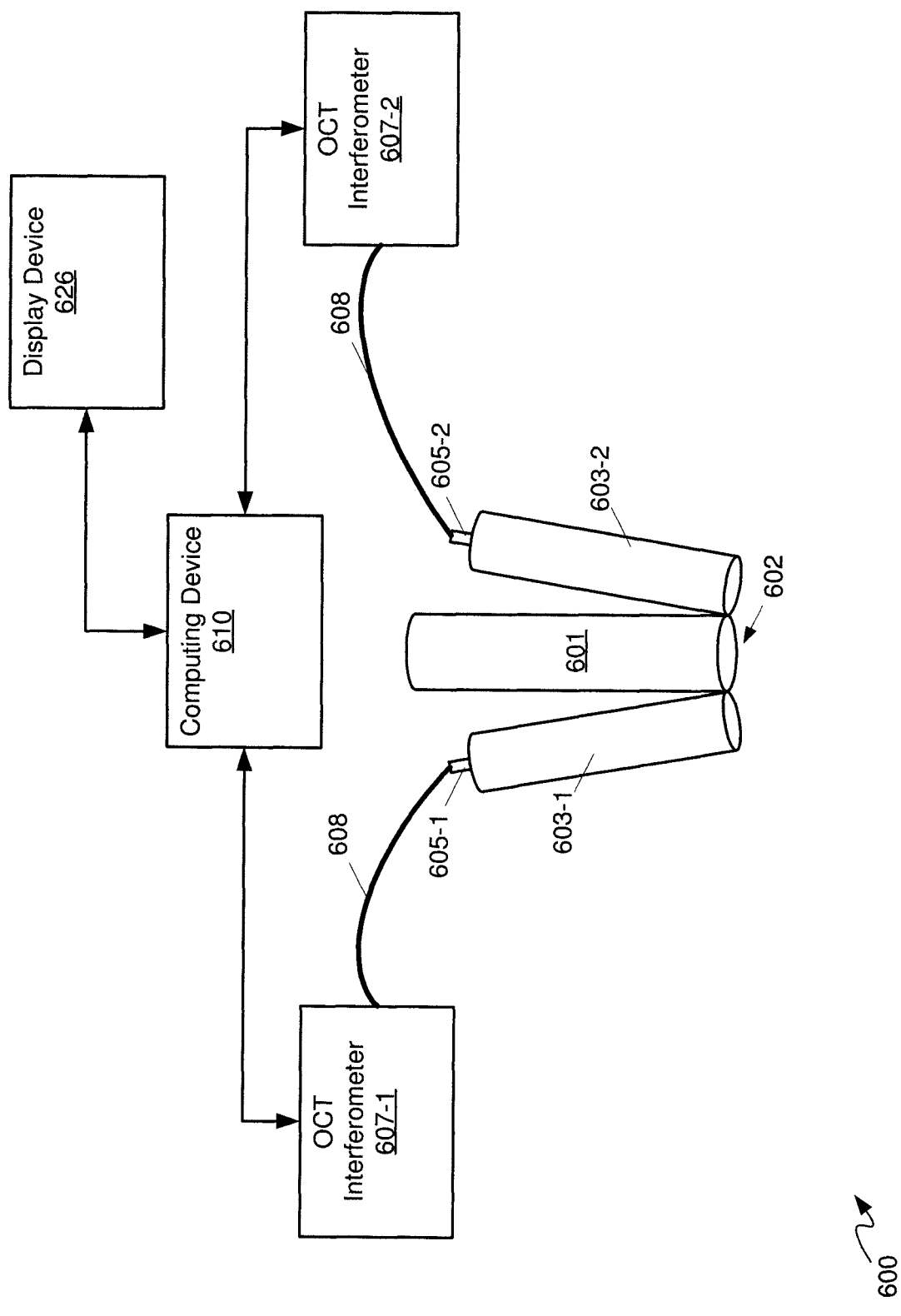
FIG. 6 depicts an OCT (Optical Coherence Tomography) system, according to non-limiting implementations.

Attention is next directed to FIG. 6, which depicts an example of a surgical tool that could be used with and/or in place of access port 12.

Specifically, FIG. 6 depicts an optical coherence tomography (OCT) system 600 comprising: a optical probe comprising a distal end 602; a first OCT probe 603-1; and, a second OCT probe 603-2, each of first OCT probe 603-1 and second OCT probe 603-2 mechanically attached to optical probe 601, first OCT probe 603-1 and second OCT probe 603-2 being substantially paraxial and configured to focus on the same scanning area, optical scope 601 configured to optically image the same scanning area using distal end 602 optical scope 601, first OCT probe 603-1 having a higher resolution than second OCT probe 603-2. First OCT probe 603-1 and second OCT probe 603-2 will be interchangeably referred to hereafter, collectively, as OCT probes 603, and generically as an OCT probe 603.

Furthermore, as depicted, system 600 further comprises a first optical coupler 605-1, a second optical coupler 605-2, a first OCT interferometer 607-1 and a second OCT interferometer 607-2, first optical coupler 605-1 configured to couple first OCT probe 603-1 to first OCT interferometer 607-1, and second optical coupler 605-2 configured to couple second OCT probe 603-2 to second OCT interferometer 607-2. First optical coupler 605-1 and second optical coupler 605-2 will be interchangeably referred to hereafter, collectively, as optical couplers 605, and generically as an optical coupler 605. Similarly, first OCT interferometer 601-1 and second OCT interferometer 607-2 will be interchangeably referred to hereafter, collectively, as OCT interferometers 607, and generically as an OCT interferometer 607.

In addition, optical communication between optical probes 603 and OCT interferometers 607 may occur using optical fibers 608. Hence, each optical coupler 605 may couple a respective OCT probe 603 to a respective OCT interferometer 607 via a respective optical fiber. Hence, each optical coupler 605 may comprise an optical fiber connector and/or coupler.

As depicted, system 600 further comprises at least one computing device 610 configured to combine output from each of first OCT probe 603-1 and second OCT probe 603-2 into combined output. In particular, system 600 further comprises at least one display device 626 in communication with computing device 610, at least one display device 626 configured to visually display the combined output from first OCT probe 603-1 and second OCT probe 603-2, as described in further detail below.

Furthermore, in the following, the terms proximal end and distal end will be used to refer to respective ends of each of optical scope 601, first OCT probe 603-1 and second OCT probe 603-2, with a proximal end being an end that will be proximal a surgeon and the like, when system 600 is in use, and a distal end being and end that will be distal the surgeon, and/or directed towards tissue, a sample, a patient being operated on, and the like, when system 600 is in use. For example, distal end 602 of optical scope 601 is an end of optical scope 601 distal a surgeon using optical scope 601.

In some implementations, optical scope 601 may be configured to optically image the same scanning area through a surgical access port. However, in other implementations, optical scope 601, first OCT probe 603-1 and second OCT probe 603-2 may be configured for use with one or more of an image guided medical procedure, and a minimally invasive procedure.

Optical scope 601 may comprise one or more of an external optical scope, a surgical microscope, and an external surgical microscope. Indeed, in some implementations, optical scope 601 may interchangeably referred to as an external optical scope, a surgical microscope, and an external surgical microscope.

Figure 7:
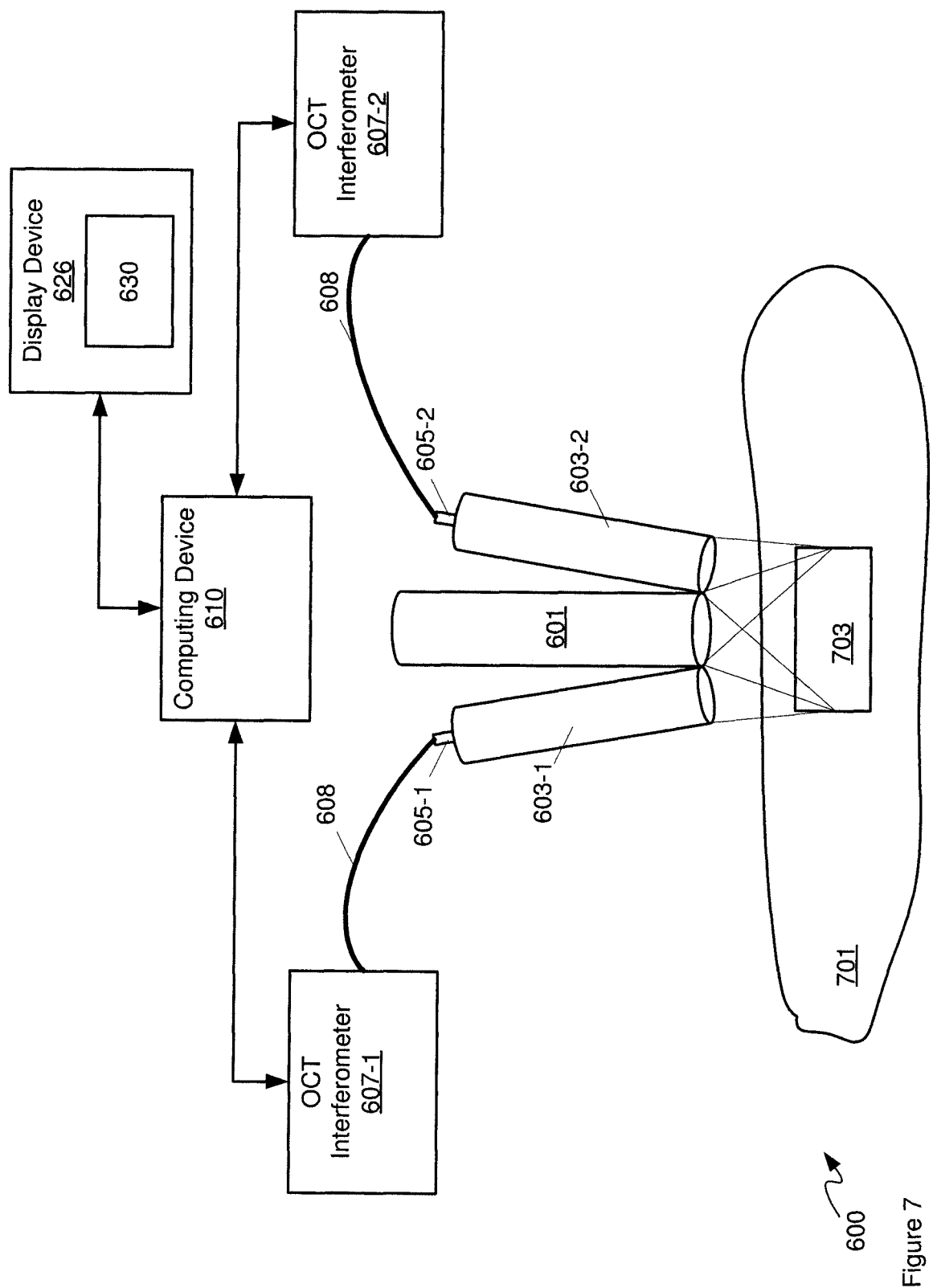
FIG. 7 depicts the OCT system of FIG. 7 in use with tissue, according to non-limiting implementations.

Attention is next directed to FIG. 7, which depicts system 600 in use, each of OCT probes 603 are generally configured to perform an OCT scan on tissue 701. For example, in use, OCT probes 603 and optical scope 601 may be positioned so that optical scope 601 may optically image tissue 701 and OCT probes 603 may perform an OCT scan on tissue 701, for example by OCT probes 603 and optical scope 601 being positioned by a device positioner system (for example see FIG. 9 described below). In some implementations, such imaging may occur through an access port and/or through aperture in a patient (e.g. as depicted in FIG. 5). OCT light, such as laser light, from respective OCT interferometers 607 is scanned across tissue 701 by each of OCT probes 603, and each OCT probe 603 collects light reflected from tissue 701. Hence, each of OCT probes 603 comprise an OCT scan lens and/or an OCT scan head that may include, but is not limited to one or more scanning components, including, but not limited to, a MEMS (microelectromechanical) mirror and a galvanometer, such scanning components configured to scan OCT light across a line and/or an area of tissue 701 to obtain a two or three dimensional OCT image respectively. Hence, each optical coupler 605 is generally configured for connection to a respective OCT interferometer 607, each optical coupler 605 generally comprising an optical connector, for example to any suitable combination of optical fibers, light guides and the like which in turn connects to a respective OCT interferometer 607.

Each OCT interferometer may comprise a light source, one or more optical couplers and/or beam splitters, and a reference arm which may comprise at least a reference mirror, and a detector. The light source may be directed to an optical coupler and/or beam splitter which splits the OCT light (e.g. laser light) into the reference arm and a sample arm. Multiple couplers can be used to split optical power between OCT probes 603 for use in power monitoring and balanced detection. In some of these implementations, OCT light provided to each of OCT probes 605 may comprise different polarization states and further used for polarization measurements. In the reference arm, the OCT light is directed to a mirror that sets a reference imaging distance from optical coupler and/or beam splitter. The OCT light then reflects back to the optical coupler and/or beam splitter. In the sample arm, the optical coupler and/or beam splitter may directs the OCT light to a respective optical coupler 605 (e.g. using a respective optical fiber) and hence a respective OCT probe 603 which, in turn, directs the OCT light to tissue 701 in an OCT scan. The respective reflected light from tissue 701 is received through a respective OCT probe 603, which directs the light back to a respective optical coupler 605, and to a respective OCT interferometer 607. The reflected light from tissue 701 and the reference mirror then interferes and forms a fringe pattern which creates an A-scan OCT signal through Fourier transform. As an OCT scan is performed by each OCT probe 603, each OCT interferometer 607 produces an OCT output, which are received by computing device 610, and combined at display device 626 in an OCT image 630.

As also depicted in FIG. 7, a same two-dimensional area 703 of tissue 701 is scanned by each of OCT probes 603. Hence, OCT image 630 of area 703 rendered at display device 626 represents the combined output from OCT probes 603. Furthermore, area 703 comprises a scanning area and/or an OCT scanning area.

Furthermore, optical scope 601 may optically image same scanning area 703 being scanned by OCT probes 603. For example, a surgeon may switch between optically imaging area 703 using optical scope 601 and imaging area 703 using OCT probes 603.

As first OCT probe 603-1 has a higher resolution than second OCT probe 603-2, first OCT probe 603-1 generally has a smaller depth of field than second OCT probe 603-2, OCT image 630 may comprise a virtual three-dimensional image of area 703. For example, in some implementations, first OCT probe 603-1 may have a resolution in a range of about 0.1 µm to about 25 µm, and in particular, a resolution in a range of about 1 µm to about 10 µm. Second OCT probe 603-2 may have a resolution in a range of about 10 µm to about 1 mm, and in particular a resolution in a range of about 25 µm to about 100 µm, as long as first OCT probe 603-1 has a higher resolution than second OCT probe 603-2, and hence a smaller depth of field. By alternating between rendering higher resolution/lower depth of field OCT images and lower resolution/higher depth of field OCT images at display device 626, a virtual three-dimensional image of area 703 is provided. Furthermore, "high resolution" OCT probe 603-1 may be used to acquire high resolution three-dimensional structural images of tissue 701 while "low resolution" OCT probe 603-2 may be used to acquire a surface contour of tissue 701.

Figure 8:
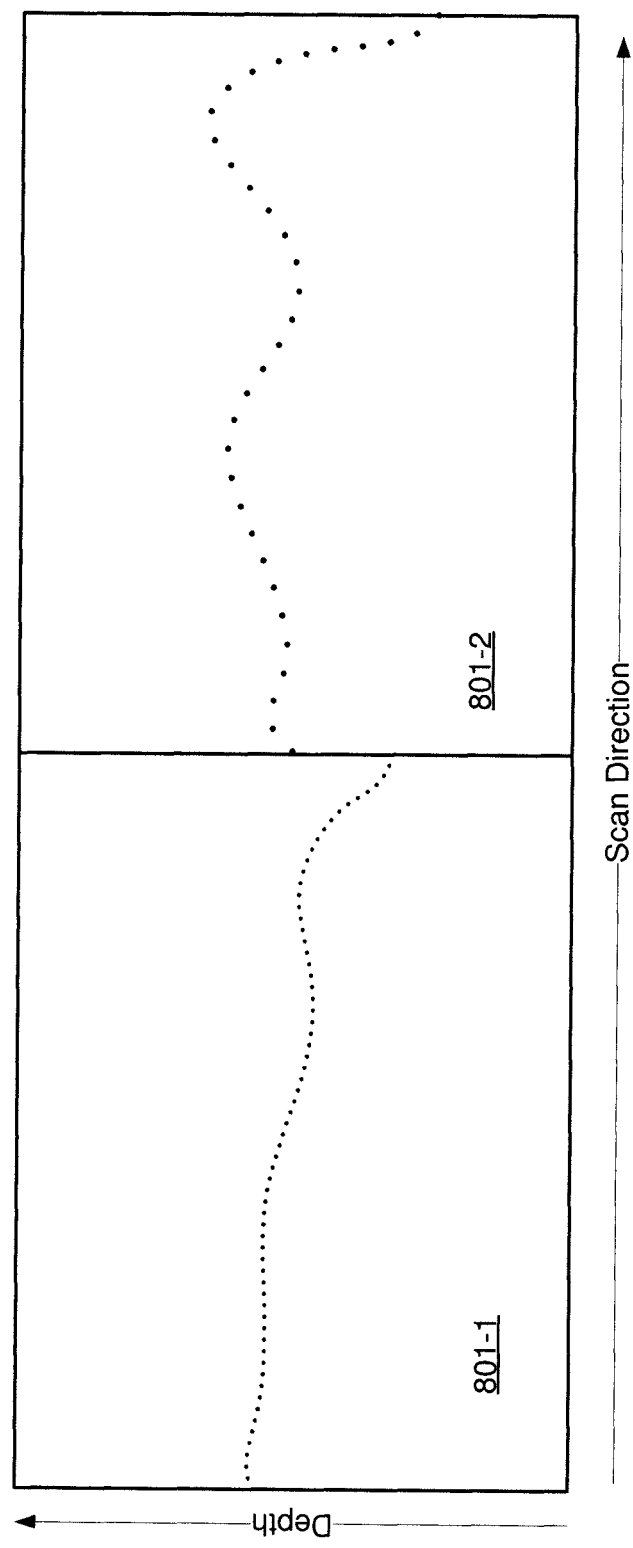
FIG. 8 depicts OCT scans acquired with a high resolution OCT probe and a low resolution OCT prove of the system of FIG. 7, according to non-limiting implementations.

Attention is next directed to FIG. 8 which depicts non-limiting example linear (i.e. one-dimensional) OCT scans from each OCT probes 603: an OCT scan 801-1 and an OCT scan 801-2 (collectively referred to as OCT scans 801 and generically as an OCT scan 801). Each OCT scan 801 is depicted schematically merely to illustrate functionality of system 600 and is not meant to represent actual OCT scans. Further, each OCT scan 801 is intended to represent an OCT scan along a same line of area 703, with OCT scan 801-1 acquired by OCT probe 603-1 and OCT scan 801-2 acquired by OCT probe 603-2. Hence, OCT scan 801-1 has a higher resolution but a smaller depth of field than OCT scan 801-2, as indicated by OCT scan 801-1 being depicted as having samples (i.e. depicted as dots) being closer together in the x-axis than OCT scan 801-2, but with OCT san 801-2 having more depth information (i.e. more information along the y-axis).

As each of OCT scan 801-1 and OCT scan 801-2 may be subsets of a two-dimensional scan of area 703, when a two-dimensional OCT of area 703 from each of OCT probes 603 are combined at OCT image 630, OCT image 630 may have a virtual three-dimensional effect.

In other words, OCT images from each of OCT probes 603 may be interlaced with each other to form OCT image 630 and/or scans of OCT images from each of OCT probes 603 may be interlaced with each other to form OCT image 630.

Figure 9:
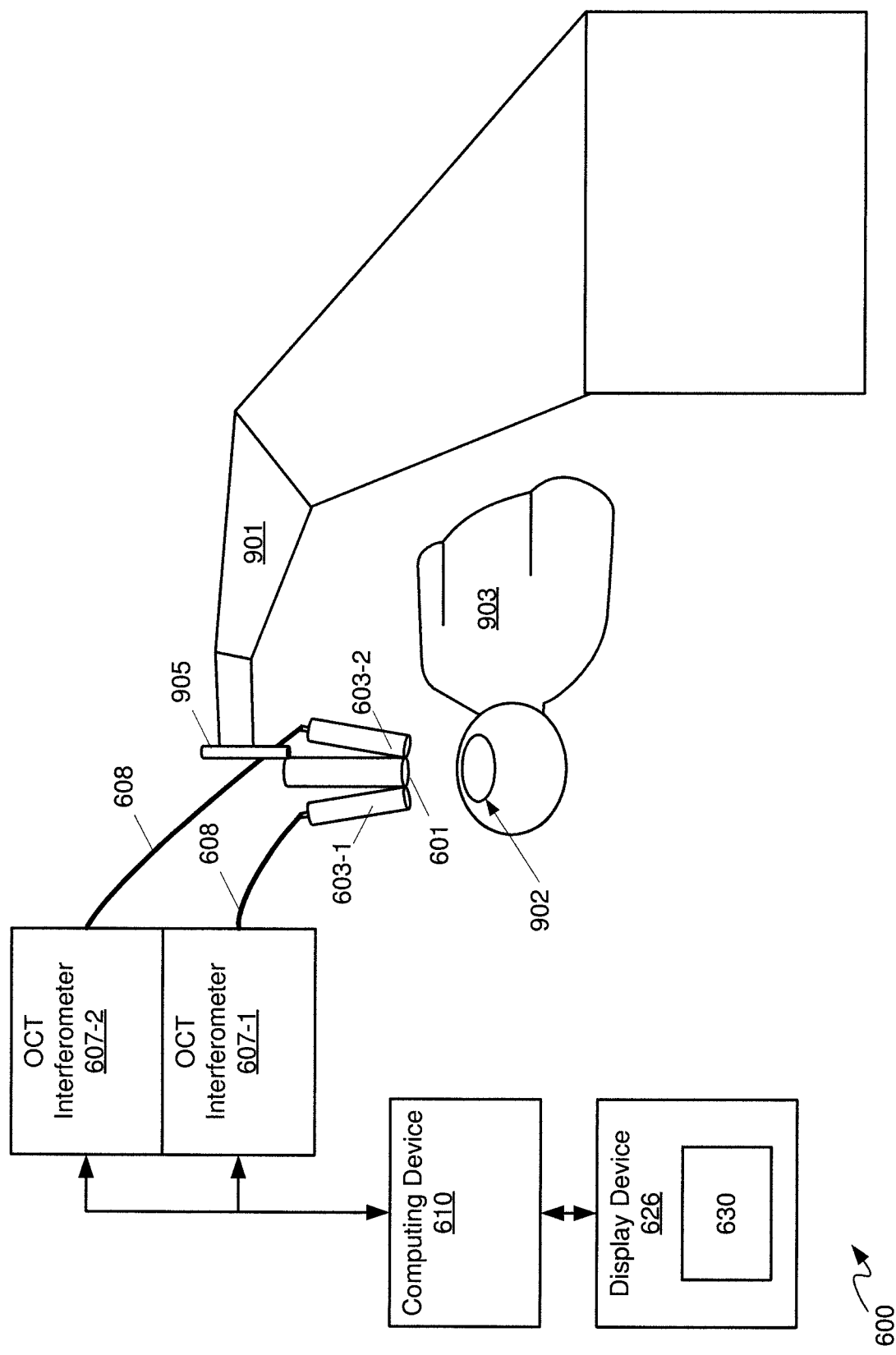
FIG. 9 depicts the OCT system of FIG. 7 in use with a patient and device positioning system, according to non-limiting implementations.

Attention is next directed to FIG. 9 which schematically depicts system 600 in use with a device positioning system 901; indeed, in some implementations system 600 may comprise device positioning system 901. In particular, a device positioning system 901 includes a coupler 905 configured to couple to one or more of optical scope 601 (as depicted) and OCT probes 603. Hence, while not depicted, system 600 may comprise one or more mechanical connectors configured to attach one or more of optical scope 601 (as depicted) and OCT probes 603 to a mechanical arm of a surgical system, for example that includes device positioning system 901.

In particular, optical scope 601 and OCT probes 603 are positioned with respect to a surgical aperture 902 that has been placed in a patient 903 (as with access port 12 in FIG. 5), so that tissue therein is accessible. In particular, device positioning system 901 may position first OCT probe 603-1 and second OCT probe 603-2 at a working distance from the tissue surface (i.e. tissue within aperture 902). Hence, device positioning system 901, may include a robotic arm, may be controlled to position optical scope 601 and OCT probes 603 relative to aperture 902 so that OCT probe 603 may perform one or more OCT scans on tissue of patient 903; for example, computing device 610 may be in communication with device positioning system 901 and control device positioning system 901, so that a OCT probes 603 are at an offset distance from tissue within tissue within aperture 902. OCT probes 603 are used to perform one or more OCT scans.

As OCT scanning and data collection may occur in real time, OCT image 630 may be updated in real time. Furthermore, the surgeon, and/or an assistant, may interact with computing device 610 (e.g. via a suitable human-machine-interface and/or an input device of computing device 610) to control which OCT images from which OCT probe 603 are being rendered at display device 626. For example, low resolution images (but with relatively high depth of field) could be rendered at display device 626 from OCT probe 603-2 to identify a region of interest of tissue as device positioning system 901 moves optical scope 601 and OCT probes 603 relative to aperture 902 and/or patient 903; and then high resolution images from OCT probe 603-2 could be rendered at display device 626 once the region of interest was identified and/or to better identify the region of interest. Alternatively, once the region of interest was identified, OCT image 630 comprising a combination of OCT images from each of OCT probes 603 could be rendered at display device 626 so that a surgeon has a virtual three-dimensional view of tissue within aperture 902. Surgical instruments could then be inserted through optical scope 601 to operate on the tissue while the tissue is being imaged using OCT probes 603.

While a particular physical configuration of each of optical scope 601 and optical probes 603 are depicted in FIGS. 6, 7 and 9, any physical configuration of each of optical scope 601 and optical probes 603 that enables optical scope 601 and optical probes 603 to be used in tandem is within the scope of present implementations, including variations in shape, relative length and the like. For example, while distal end 602 of optical scope 601 is depicted as not extending past respective ends of OCT probes 603, in other implementations a distal end of optical scope 601 may extend past respective ends of OCT probes 603 so that the distal end of optical scope 601 could be inserted into aperture 902.

Furthermore, while in FIGS. 6, 7 and 9 first OCT probe 603-1 and second OCT probe 603-1 are attached on opposite sides of optical scope 601, in other implementations, may be attached in any manner where they are paraxial.

Indeed, it should be understood that implementations described herein may be susceptible to various modifications and alternative forms. For example, in some implementations, first OCT probe 603-1 and second OCT probe 603-2 are mechanically attached to optical scope 601 using any suitable fasteners, epoxies, glues, welds and the like. In some implementations, one or more of first OCT probe 603-1 and second OCT probe 603-2 are may be removable from optical scope 601, using suitable fasteners, couplers and the like, while in other implementations one or more of first OCT probe 603-1 and second OCT probe 603-1 may be permanently attached to optical scope 601. When one or more of first OCT probe 603-1 and second OCT probe 603-2 is removable from optical scope 601, an attachment apparatus may be configured to removably attach one or more of first OCT probe 603-1 and second OCT probe 603-2 at a respective angle to surgical port so that first OCT probe 603-1 and second OCT probe 603-2 are paraxial.

Figure 10:
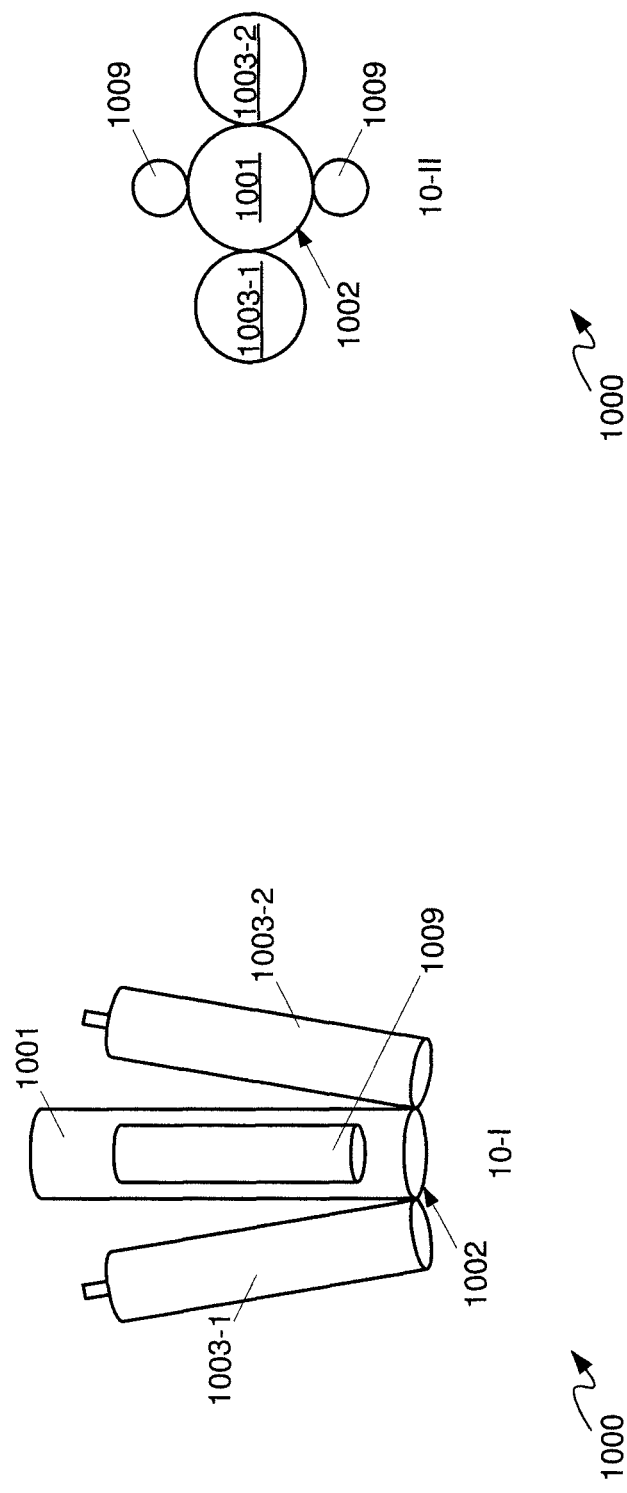
FIG. 10 depicts an alternate implementation of a optical scope and OCT probes combined with illuminators, according to alternative non-limiting implementations.

As a further example of non-limiting alternative implementations, attention is next directed to FIG. 10 which depicts a perspective views 10-I, and a distal end view 10-II of a system 1000 comprising: an optical scope 1001 comprising a distal end 1002; a first OCT probe 1003-1; and, a second OCT probe 1003-2, each of first OCT probe 1003-1 and second OCT probe 1003-2 mechanically attached to optical scope 1001, first OCT probe 1003-1 and second OCT probe 1003-2 being substantially paraxial and configured to focus on a same scanning area, optical scope 1001 configured to image the same scanning area using distal 1002 end, first OCT probe 1003-1 having a higher resolution than second OCT probe 1003-2. First OCT probe 1003-1 and second OCT probe 1003-2 will be interchangeably referred to hereafter, collectively, as OCT probes 1003, and generically as an OCT probe 1003. Optical scope 1001 and OCT probes 1003 are hence respectively similar to optical scope 601 and OCT probes 603. However, system 1000 further comprises at least one illuminator 1009 configured to illuminate the same scanning area, for example when optical scope 1001 is being used in an optical mode and/or when surgical tools are being inserted through optical scope 1001. For example, as is best seen in view 10-II, as depicted system 1000 comprises two illuminators 1009 on opposite sides of optical scope 1001, alternating circumferentially with OCT probes 1003 around optical scope 1001, which may be connected, for example to computing device 610 and/or a power source (and a switch) such that one or more of illuminators 1009 may be turned on to illuminate a scanning area. Hence, when a surgeon, and the like is optically imaging tissue and/or a scanning area using optical scope 1001, illuminators 1009 may be used to illuminate an area being optically imaged, which may comprise the scanning area of optical probes 1003. While two illuminators 1009 are depicted in FIG. 10, in other implementations system 1000 may comprise fewer than two illuminators 1009, while in yet further implementations, system 1000 may comprise more than two illuminators 1009. Furthermore, system 600 may be adapted to include illuminators.

Each illuminator 1009 may comprise a light source including, but not limited to, a light emitting diode (LED) light source).

Figure 11:
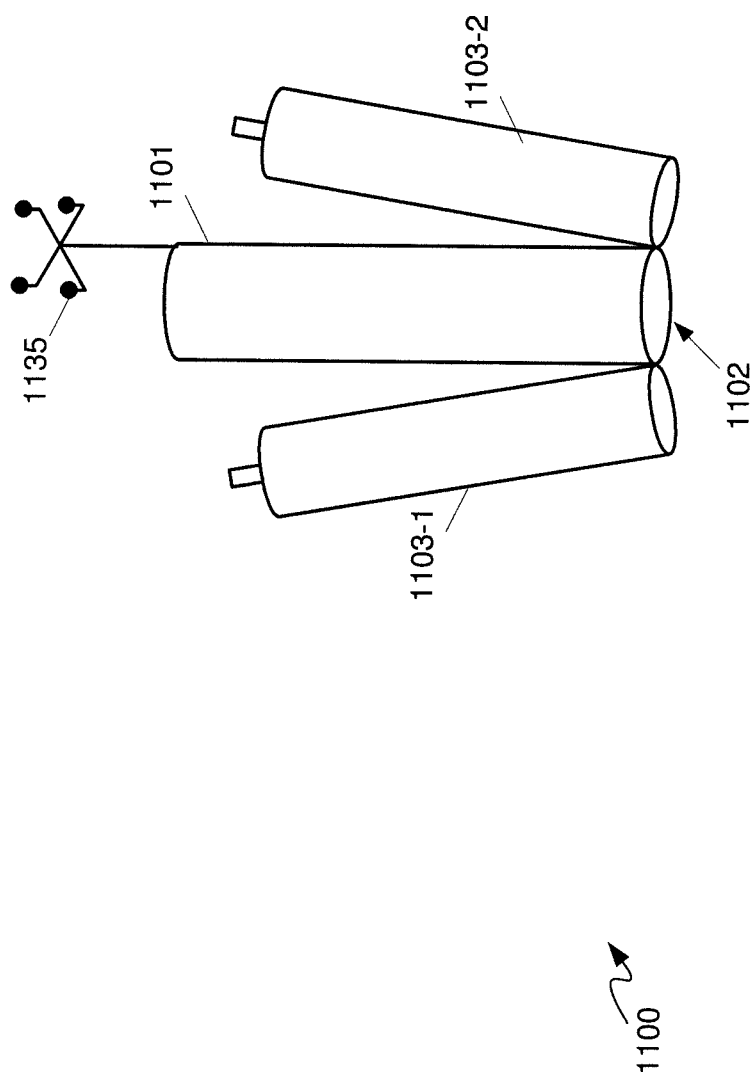
FIG. 11 depicts an alternate implementation of a optical scope and OCT probes combined with a tracking device, according to alternative non-limiting implementations.

As yet a further example of non-limiting alternative implementations, attention is next directed to FIG. 11 which depicts a perspective views 11-I, and a distal end view 11-II of a system 1100 comprising: an optical scope 1101 comprising a distal end 1102; a first OCT probe 1103-1; and, a second OCT probe 1103-2, each of first OCT probe 1103-1 and second OCT probe 1103-2 mechanically attached to optical scope 1101, first OCT probe 1103-1 and second OCT probe 1103-2 being substantially paraxial and configured to focus on a same scanning area, optical scope 1101 configured to optically image the same scanning area using distal end 1102, first OCT probe 1103-1 having a higher resolution than second OCT probe 1103-2. First OCT probe 1103-1 and second OCT probe 1103-2 will be interchangeably referred to hereafter, collectively, as OCT probes 1103, and generically as an OCT probe 1103. Optical scope 1101 and OCT probes 1103 are hence respectively similar to optical scope 601 and OCT probes 603.

However, in contrast to system 600, system 1100 further comprises a tracking device 1135 located at proximal end of OCT system 1100 and in particular a proximal end of optical scope 1101, the proximal end of optical scope 1101 located opposite distal end 1102; alternatively tracking device 1135 could be located a proximal end of either of optical probes 1103. Tracking device 1135 is generally configured to be tracked by a navigation system external to OCT system 1100. While not depicted one or more of optical scope 1101 and OCT probes 1103 may further comprise a mount configured to removably attach tracking device 1135 at a respective proximal end. Tracking device 1135 is generally to extend away from one or more of optical scope 1101 and OCT probes 1103 so that a camera, and the like, of a surgical navigation system may track a position of tracking device 1135 and hence a position of one or more of optical scope 1101 and OCT probes 1103. As depicted, tracking device 1135 comprises four reflective spheres arranged in a configuration where each sphere is located at about a corner of a square. However, other numbers of spheres and other configurations are within the scope of present implementations. In particular or more of a number, arrangement, and configuration of such spheres may be selected to provide a given tracking accuracy, including, but not limited to, a tracking accuracy that is less than about half a diameter of a sensing array surface. However, tracking device 1135 may include tracking devices other than reflective spheres. For example, in some implementations, tracking device 1135 may include a flexible sheath configured to measure tip position deflection, for example deflection of a tip of the flexible sheath. Furthermore, system 600 may be adapted to include one or more tracking devices.

Figure 12:
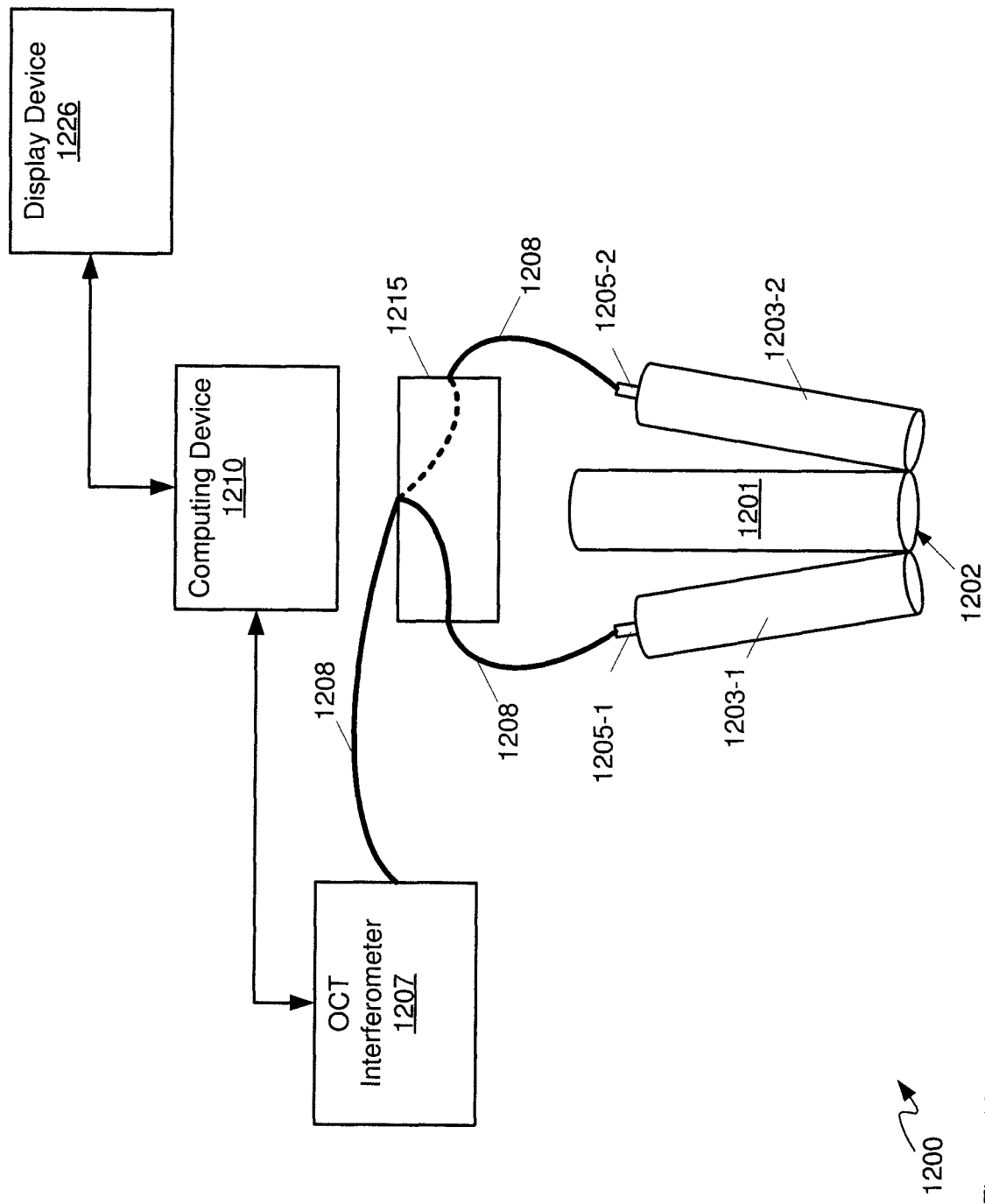
FIG. 12 depicts an OCT system that includes a switchable optical coupler, according to alternative non-limiting implementations.

Alternative optical configurations of system 600 are also within the scope of present implementations. For example, attention is next directed to FIG. 12, which is substantially similar to FIG. 6, with like components having like numbers, but in a "1200" series rather than a "600" series. Hence, FIG. 12 depicts an OCT system 1200 which comprises: a optical scope 1201 comprising a distal end 1202; a first OCT probe 1203-1; and, a second OCT probe 1203-2, each of first OCT probe 1203-1 and second OCT probe 1203-12 mechanically attached to optical scope 1201, first OCT probe 1203-1 and second OCT probe 1203-2 being substantially paraxial and configured to focus on a same scanning area, optical scope 1201 configured to optically image the same scanning area using distal end 1202, first OCT probe 1203-1 having a higher resolution than second OCT probe 1203-2. First OCT probe 1203-1 and second OCT probe 1203-2 will be interchangeably referred to hereafter, collectively, as OCT probes 1203, and generically as an OCT probe 1203.

System 1200 further comprises: a first optical coupler 1205-1, a second optical coupler 1205-2, and an OCT interferometer 1207 in optical communication with each other via optical fibers 1208 and an optical coupler 1215 configured to switch between coupling first OCT probe 1203-1 or second OCT probe 1203-2 to OCT interferometer 1207.

As depicted, system 1200 further comprises at least one computing device 1210 configured to receive data from OCT interferometer 1207 and render the data at least one display device 1226.

In particular optical coupler 1215 may switch between relaying OCT data from OCT probes 1203 to OCT interferometer; for example, optical coupler 1215 may comprises an optical rotary joint. Hence, by mechanically adjusting optical coupler 1215, an optical path from OCT interferometer 1207 may be switched from OCT probe 1203-1 to OCT probe 1203-2. As depicted, OCT interferometer 1207 is in optical communication with OCT probe 1203-1; however, as schematically represented by the stippled line within optical coupler 1215, optical coupler 1215 may be adjusted to change optical communication between OCT interferometer 1207 and OCT probe 1203-2. Hence, in contrast to system 600, system 1200 comprises one OCT interferometer 1207 which is shared between OCT probes 1203.

Such adjustment may occur manually in some implementations and/or under control of computing device 1210 in other implementations. Hence, a surgeon may switch being displaying a high resolution OCT image and a low resolution OCT image at display device 1226 by using optical coupler 1215 to switch between OCT probe 1203-1 and OCT probe 1203-2.

Yet further alternative optical configurations of system 600 are also within the scope of present implementations. For example, attention is next directed to FIG. 13, which is substantially similar to FIG. 6, with like components having like numbers, but in a "1300" series rather than a "600" series. Hence, FIG. 13 depicts an OCT system 1300 which comprises: an optical scope 1301 comprising a distal end 1302; a first OCT probe 1303-1; and, a second OCT probe 1303-2, each of first OCT probe 1303-1 and second OCT probe 1303-13 mechanically attached to optical scope 1301, first OCT probe 1303-1 and second OCT probe 1303-2 being substantially paraxial and configured to focus on a same scanning area, optical scope 1301 configured to optically image the same scanning area using distal end 1302, first OCT probe 1303-1 having a higher resolution than second OCT probe 1303-2. First OCT probe 1303-1 and second OCT probe 1303-2 will be interchangeably referred to hereafter, collectively, as OCT probes 1303, and generically as an OCT probe 1303. As depicted, system 1300 further comprises at least one computing device 1310 configured to receive data from OCT interferometer 1307 and render the data at least one display device 1326.

System 1300 further comprises: a first optical coupler 1305-1, a second optical coupler 1305-2, and an OCT interferometer 1307 in optical communication with each other via optical fibers 1308 and an optical coupler 1315 configured to optically couple first OCT probe 1303-1 and second OCT probe 1303-2 to the same OCT interferometer 1307, for example using an optical fiber coupler.

However, in contrast to system 1200, system 1300 further comprises a switchable cover 1350 configured to alternately cover first OCT probe 1303-1 and second OCT probe 1303-2, for example at a respective distal end of each of OCT probes 1303. As depicted, switchable cover 1350 is depicted as covering a distal end of first OCT probe 1303-1, with a second position of switchable cover 1350 covering a distal end of second OCT probe 1303-2 in stippled lines. While positions of switchable cover 1350 are depicted schematically, switchable cover 1350 may comprise components configured to move switchable cover 1350 between the positions; such components may include, but are not limited to, rails, wheels, gears, and the like. Furthermore, motion of switchable cover 1350 between positions may be linear and/or circular and/or any other mode which enables switchable cover 1350 to be moved between positions.

Hence, a surgeon may switch being displaying a high resolution OCT image and a low resolution OCT image at display device 1326 by using switchable cover 1350 alternately block OCT probe 1303-2 and OCT probe 1303-1.

While features of OCT probes described with reference to specific implementations, features described with reference to one implementation of an OCT probe may be used with other implementations of OCT probes. For example, any of the OCT probes described herein may be adapted to include anti-reflective coatings, immersion materials, index matching materials, tracking devices, and the like.

Described herein is are implement systems that include OCT probes which planarize material in a scan plane of an OCT scan lens using a transparent material which may result in a reduction and/or elimination of mirror artifacts.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An OCT (Optical Coherence Tomography) system comprising:
    an optical scope comprising a distal end;
    a first OCT probe;
    a second OCT probe, each of the first OCT probe and the second OCT probe mechanically attached to the optical scope, the first OCT probe and the second OCT probe being substantially paraxial and configured to focus on a same scanning area, the optical scope configured to optically image the same scanning area using the distal end, the same scanning area including a tissue surface, wherein the second OCT probe has a larger depth of field than the first OCT probe, the second OCT probe having a lower resolution than the first OCT probe such that the first OCT probe acquires structural images of the tissue surface, and the second OCT probe having a larger field-of-view than the first OCT probe, such that the second OCT probe acquires a surface contour of the tissue surface,
    wherein the optical scope is configured to image the same scanning area through a surgical access port, and the first OCT probe and the second OCT probe are configured to scan the same scanning area through the surgical access port;
    at least one OCT interferometer;
    a first optical coupler configured to optically couple the first OCT probe to the at least one OCT interferometer;
    a second optical coupler configured to optically couple the second OCT probe to the at least one OCT interferometer;
    at least one computing device configured to: combine output from each of the first OCT probe and the second OCT probe into combined output; and
    at least one display device in communication with the at least one computing device, the at least one display device configured to visually display the combined output from the first OCT probe and the second OCT probe,
    the at least one computing device further configured to:
        control the at least one display device to first render low resolution images from the second OCT probe to identify a region of interest including the surface contour of the tissue surface;
        then render high resolution images of the region of interest from the first OCT probe including the structural images of the tissue surface; and, thereafter,
        control the at least one display device to alternate between rendering higher resolution/lower depth of field OCT images, including the structural images of the tissue surface and lower resolution/higher depth of field OCT images including the surface contour of the tissue surface, to render a virtual three-dimensional image of the same scanning area.

2. The OCT system of claim 1, wherein the optical scope, the first OCT probe and the second OCT probe are configured for use with one or more of an image guided medical procedure, and a minimally invasive procedure.

3. The OCT system of claim 1, wherein the at least one OCT interferometer includes a first OCT interferometer and a second OCT interferometer, the first optical coupler configured to couple the first OCT probe to the first OCT interferometer, and the second optical coupler configured to couple the second OCT probe to the second OCT interferometer.

4. The OCT system of claim 1, further comprising an optical coupling device, and wherein the at least one OCT interferometer comprises a single OCT interferometer, the optical coupling device configured to switch between coupling the first OCT probe or the second OCT probe to the single OCT interferometer.

5. The OCT system of claim 4, wherein the optical coupling device comprises an optical rotary joint.

6. The OCT system of claim 1, further comprising at least one illuminator configured to illuminate the same scanning area.

7. The OCT system of claim 1, wherein each of the first OCT probe and the second OCT probe are removable from the optical scope.

8. The OCT system of claim 1, wherein the first OCT probe and the second OCT probe are attached on opposite sides of the optical scope.

9. The OCT system of claim 1, further comprising a mechanical connector configured to attach one or more of the optical scope, the first OCT probe and the second OCT probe to a mechanical arm of a surgical system.

10. The OCT system of claim 1, further comprising a tracking device located at a proximal end of the OCT system, the tracking device configured to be tracked by a navigation system.

11. The OCT system of claim 1, further comprising a device positioning system that positions the optical scope, the first OCT probe and the second OCT probe at a working distance from the tissue surface.

12. The OCT system of claim 1, wherein the first OCT probe has a resolution in a range of about 0.1 μm to about 25 μm, and the second OCT probe has a respective resolution in a range of about 10 μm to about 1 mm.

13. The OCT system of claim 12, wherein the first OCT probe has a resolution in a range of about 1 μm to about 10 μm, and the second OCT probe has a respective resolution in a range of about 25 μm to about 100 μm.

* * * * *